United States Patent
Headley

(10) Patent No.: US 12,427,217 B2
(45) Date of Patent: Sep. 30, 2025

(54) DISINFECTANT DISTRIBUTION SYSTEM

(71) Applicant: Andrew Headley, Buford, GA (US)

(72) Inventor: Andrew Headley, Buford, GA (US)

( * ) Notice: Subject to any disclaimer, the term of this patent is extended or adjusted under 35 U.S.C. 154(b) by 652 days.

(21) Appl. No.: 16/907,413

(22) Filed: Jun. 22, 2020

(65) Prior Publication Data

US 2021/0393836 A1 Dec. 23, 2021

(51) Int. Cl.
*B05B 9/03* (2006.01)
*A61L 2/18* (2006.01)
*A61L 2/26* (2006.01)
*B05B 9/04* (2006.01)
*B05B 15/62* (2018.01)
*B05B 15/65* (2018.01)

(52) U.S. Cl.
CPC ........ *A61L 2/26* (2013.01); *A61L 2/18* (2013.01); *B05B 9/035* (2013.01); *B05B 9/04* (2013.01); *B05B 15/62* (2018.02); *B05B 15/65* (2018.02); *A61L 2202/15* (2013.01); *A61L 2202/16* (2013.01); *A61L 2202/25* (2013.01)

(58) Field of Classification Search
CPC ......... B05B 15/62; B05B 15/65; B05B 9/035; B05B 9/04; A61L 2/18; A61L 2202/15; A61L 2202/25

See application file for complete search history.

(56) References Cited

U.S. PATENT DOCUMENTS

| 2010/0219258 A1* | 9/2010 | Starcic | A61L 2/22 239/289 |
| 2020/0242575 A1* | 7/2020 | Shell | A61L 2/22 |

FOREIGN PATENT DOCUMENTS

| CN | 108096615 A | * | 6/2018 | ............ A61L 2/22 |
| CN | 110124891 A | * | 8/2019 | |
| CN | 111215266 A | * | 6/2020 | |
| KR | 101118502 B1 | * | 3/2012 | ......... A61L 2202/15 |
| WO | WO-2010026416 A1 | * | 3/2010 | ............ A61L 2/10 |
| WO | WO-2011072087 A1 | * | 6/2011 | ............ A61L 2/10 |
| WO | WO-2018020716 A1 | * | 2/2018 | ......... A61B 1/00057 |

OTHER PUBLICATIONS

Translation of CN 111215266 A, 2020 (Year: 2020).*
Translation of CN 110124891 A, 2019 (Year: 2019).*
CN-108096615-A_Translation.*
CN-108096615-A_translation (Year: 2018).*
Lumax—LX-1361 Diaphragm Pump, 110-120V, Aug. 10, 2017, Lumax, https://www.lumax.com/lx-1361 (Year: 2017).*
KR_101118502_B1_translation (Year: 2012).*

* cited by examiner

*Primary Examiner* — Elizabeth A Robinson
*Assistant Examiner* — Changru Chen
(74) *Attorney, Agent, or Firm* — Ron Baker, Esq.; BAKER & CO. PATENT LAW

(57) ABSTRACT

The present invention is a disinfectant distribution system for conveniently eliminating viruses and diseases. In particular, the invention allows a user to conveniently install the system in public and private spaces to help improve life. The proposed embodiment provides a unique experience for a user by providing a safe experience for the general public.

12 Claims, 3 Drawing Sheets

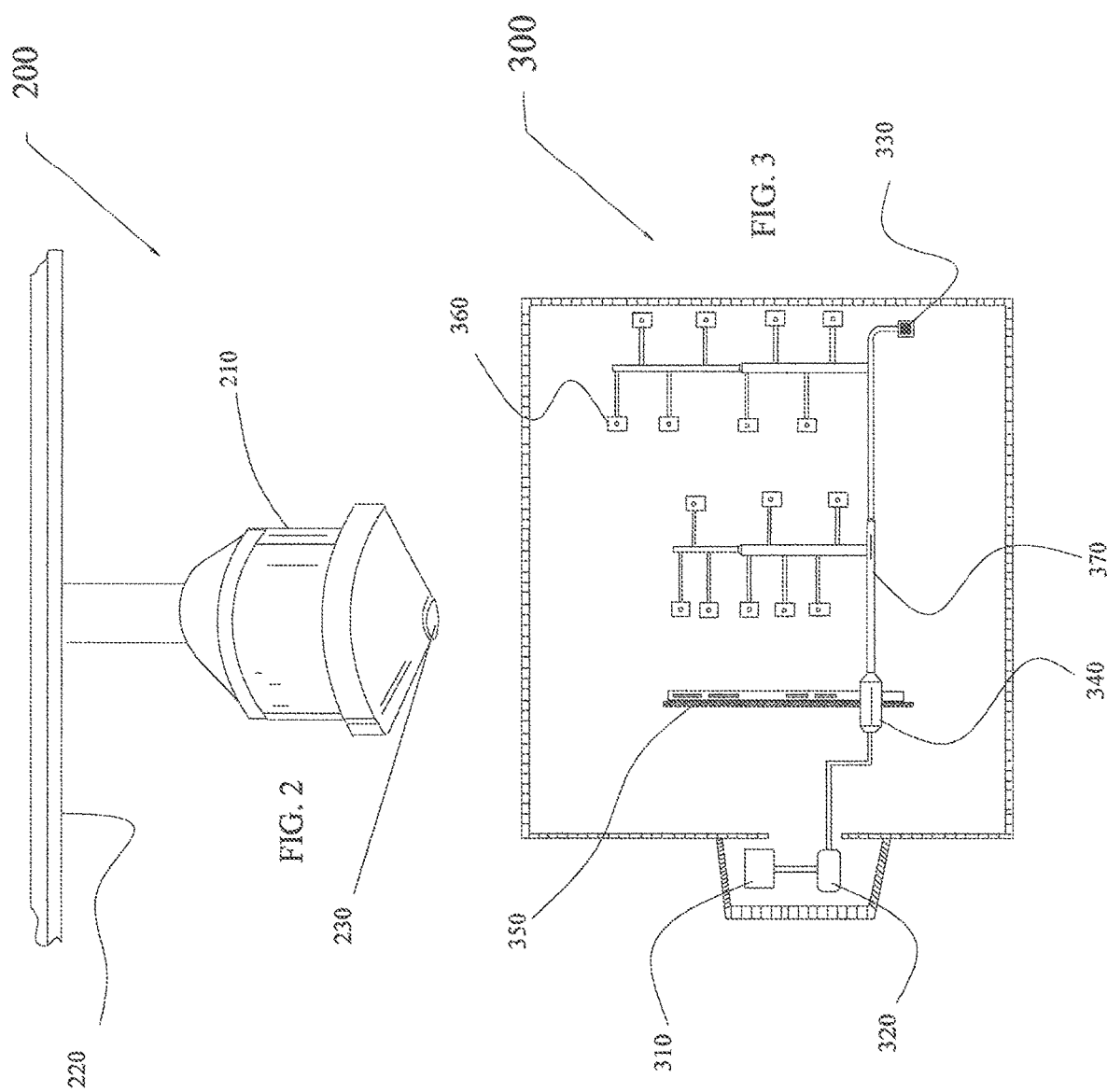

DISINFECTANT DISTRIBUTION SYSTEM

CROSS-REFERENCE TO RELATED APPLICATIONS

None.

BACKGROUND OF THE INVENTION

Field of the Art

The disclosure relates to a system for disinfecting an interior commercial space, and more particularly the invention is a system that provides a method for disinfecting surrounding areas. The embodiment allows a user to effectively kill viruses and diseases in public places where a large number of people congregate.

Discussion of the State of the Art

Commercial facilities include places such as grocery stores, movie theaters, and malls that allow the general public to shop but are considered a heightened risk for health concerns due to exposure associated to pathogens. These facilities often include thousands of individuals who may be suffering from domestic and foreign illnesses that can quickly spread to others. Most large metropolitan areas in the U.S. Include a significant amount of the public shopping at grocery stores throughout the week and especially during the weekend. Historically, these stores are becoming more communal with people socializing more around coffee bars and the like. U.S. News & World Report stated that a typical grocery cart handle could be home to 11 million microorganisms, including some from raw meat. Furthermore, in the case of malls even if you aren't standing right next to someone who's carrying pathogens, you are potentially touching clothing and other items that an infected person touched or coughed on. And that's even before you get hungry and indulge in some mall food, which was potentially prepared by someone carrying the virus. Utilizing public spaces in this manner can eventually pose a threat to the public since complex and deadly viruses are a reality among our society. Accordingly, what is needed in the art is a novel manner of disinfecting public spaces to create a safer environment for patrons. What is further needed in the art is a novel invention that will kill airborne viruses and diseases in public venues to ensure the safety and health of the public. The proposed embodiment is further ideal because its ultimate purpose is to allow users to keep their public spaces safe in a manner that will be a welcoming change for patrons.

SUMMARY OF THE INVENTION

Accordingly, the inventor has conceived, in a preferred embodiment of the invention, a disinfectant distribution system for public use.

According to a preferred embodiment of the invention, is a disinfectant system that allows the user to kill viruses in an isolated environment, in a novel manner. What is further disclosed is a disinfectant system that provides a way for the user to easily install a disinfectant distribution system in a commercial space that will provide a virus free area. What is further disclosed is a distribution system that can be retrofitted to fit public facilities. The flexibility and distribution of the system is a key component of the invention in that it provides the user the ability to disinfect various public areas no matter the configuration.

The objects and advantages of the present invention will become apparent to those skilled in the art when the following description of examples of structure representing the best modes contemplated at the present for practicing the invention is read in conjunction with the accompanying drawing wherein like references numerals refer to like or equivalent parts.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary and are not to be considered as limiting of the scope of the invention or the claims herein in any way.

FIG. 2 is a schematic view of a nozzle, according to a preferred embodiment of the invention.

FIG. 3 is a top-view of a disinfectant distribution system, according to a preferred embodiment of the invention.

DETAILED DESCRIPTION

Figure 1:
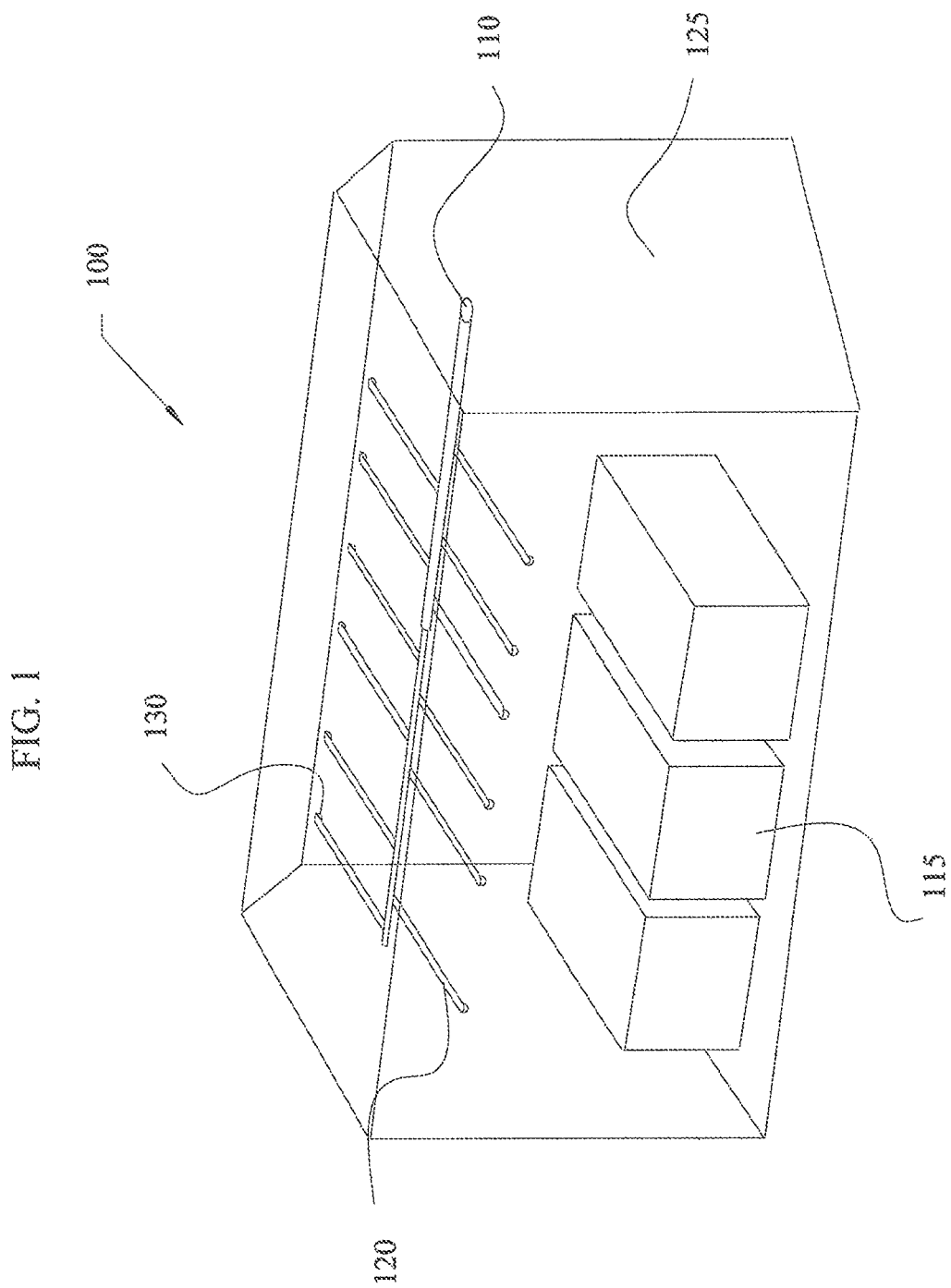
FIG. 1 is a perspective view of an installed nozzle system of the disinfectant distribution system, according to a preferred embodiment of the invention.

The inventor has conceived, a system for eliminating viruses and diseases on surfaces and the surrounding environment in a convenient manner.

The terms "a" or "an", as used herein, are defined as one, or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an exemplary embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Thus, the appearances of such phrases or in various places throughout this specification are not necessarily all referring to the same embodiment.

Numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only and are not to be taken as limiting the disclosure in any way.

A description of an embodiment with several components in connection with each other does not imply that all such components are required. To the contrary, a variety of optional components may be described to illustrate a wide variety of possible embodiments of one or more of the inventions and in order to more fully illustrate one or more aspects of the inventions.

Materials described or referenced herein will sometimes be described in singular form for clarity. However, it should be appreciated that particular embodiments may include multiple instantiations of a material unless noted otherwise. Surfaces in some embodiments can be understood as representing segments or portions of those embodiments. Alternate implementations are included within the scope of embodiments of the present invention would be understood by those having ordinary skill in the art.

Definitions

Reference throughout this document to "detachable cornice", or similar terms refers to a structure that mounts horizontally where necessary to secure the distribution system. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to "trave", or similar terms refers to various cross bars that will be utilized to install the distribution system. The cross bars are detachable and can be removed while not in use or interchanged where larger cornices are needed for specific tasks. Thus, the appearances of such phrases or in various places throughout this specification are not necessarily all referring to the same embodiment.

Reference throughout this document to "tuyere", "exhaust pipes", or similar terms refers to air pipes that can be utilized with the embodiment. Thus, the appearances of such phrases or in various places throughout this specification are not necessarily all referring to the same embodiment.

In an embodiment, the Disinfectant Distribution System™ is designed to provide a unique and novel manner for a user to eliminate harmful pathogens that may cause a threat to the public. The Disinfectant Distribution System™ is designed with various nozzles conveniently located along a piping system that will be mounted throughout a given space. Where there are public spaces that allow a large number of people to congregate it should be appreciated that the Disinfectant Distribution System™ will be designed to eliminate the spread of diseases and viruses that can be spread over both air or surfaces. This ability will provide the user with broader options to keep their environment safe for the public.

In an alternate embodiment, if a user's existing public space does not currently have such a distribution system, the present invention will allow users to easily install the system. To further illustrate, the Disinfectant Distribution System™ has attachment devices that allows a user to easily install for effective use. The embodiment includes cornices and other brackets that allow the system to be installed utilizing a number of traves and attachment members. To illustrate, the user can utilize a three-part system for installing the embodiment to form a system that can be suspended over a designated area to eliminate viruses for instance. The embodiment's three part-system includes the main piping system, detachable cornice attachment, and the compressor/chemical storage. In essence, the user will be able to install the embodiment in a convenient manner and initiate the distribution system. Due to the embodiment's ideal three-part system, the embodiment can be configured to overcome any existing obstacle during the installation.

In an embodiment, the Disinfectant Distribution System™ has the ability to fit into a designated public space depending on the configuration of the area. The system is uniquely configured to allow the attachment platform of the embodiment to be coupled with either existing points or easily connected detachable cornices that come standard with the embodiment. The Disinfectant Distribution System™ will be attached to the overhead cornice system for suspending the piping system for targeted dispensing in designed areas. Users will appreciate the numerous nozzles that are aligned throughout the piping system in a uniform fashion. The nozzles are equally distanced throughout the pipes to dispense a mist of safe disinfectant throughout the surrounding area. The pressure can be adjusted to allow the user to cover critical areas during operation.

In a non-limiting example, the embodiment may be designed in various widths and lengths to satisfy a user's preference. For instance, where a user utilizes a commercial shopping area for selling vehicles that is typically much larger than an area used for clothing for instance then the distribution system can be designed to accommodate larger areas.

Referring to the drawings, and more particularly to FIG. 1, there is illustrated, schematically, a disinfectant distribution system 100 comprising a supply pipe system 110 configured in a designated area 125 for disinfecting pathogens. A mixture of disinfectant is supplied to the designated area 125 by a supply piping system 110 to a target object 115 when the mixture is transferred through the piping system 110 and eventually dispensed by the nozzles 130. The combination of the supply pipes and the nozzles 130 make up the body of the embodiment which operates to distribute the disinfectants to the target object 115.

In an exemplary embodiment, the embodiment of FIG. 2, there is illustrated, an exploded view of a single nozzle 210 that is attached to the piping system 220. The pipes are attached to an adjacent top mounting surface utilizing a series of mounts that are attached to both the pipes, cornices, and the top mounting surface to hold the pipes in place. The schematic further illustrates the nozzle opening 230 where the disinfectant is dispensed. FIG. 3 illustrates a top-view of a designated area 300 to include an electronically driven compressor 310 that is connected to chemical storage unit 320 and is coupled to an enjoining pipe 370 that is connected to a one-way valve 340 to allow the distribution of the disinfectant. The nozzles 360 are connected to a system of air pipes made of a number of industry standard material. In a non-limiting example, the pipe system 370 can be designed by utilizing PVC piping material that is considered economical in the art. The embodiment will be installed by utilizing a detachable cornice 350 to secure the distribution system. The system will have at least one control unit 330 and at least one chemical storage unit 320 for liquid and powder storage. The amount of chemical storage will be determined on the quantity of disinfectant needed for a given area of space. The chemical storage unit 320 will be designed to be stored in a remote location for maintenance accessibility. In an ideal condition, a remote location can be a storage area near the installation point. The embodiment will also be capable of connecting to an external electrical compressor that may be located outside a designated building. To elaborate, the embodiment can be designed in a manner to run an electrical line from the distribution system to an outside compressor for greater options for the user. It will be appreciated that the current embodiment can be designed to utilize all forms of energy such as gas, electric, and solar but are not limited to these examples. Furthermore, the embodiment is not dependent on low voltage energy but rather can be powered by regular or line voltage energy as well, and may utilize power sources driven by various types of fuels such as diesel, ethanol, methanol, gasoline etc. but is not limited by these examples.

In a non-limiting example, a given cup of powder may be required for a certain volume of water. The control unit 330 is designed from a number of process control systems designs that will allow the user to manage the embodiment from multiple locations utilizing a computer control system. In a non-limiting example, the control unit will include a lock-out capability to allow for safety measures and prevent unauthorized use by third parties. The lock-out system can include a combination of physical locking mechanisms operated manually or system locks that will be driven through internal software. Generally, the control unit will be installed along a wall or against a similar structure to allow the user to gain access to the control unit.

Figure 4:
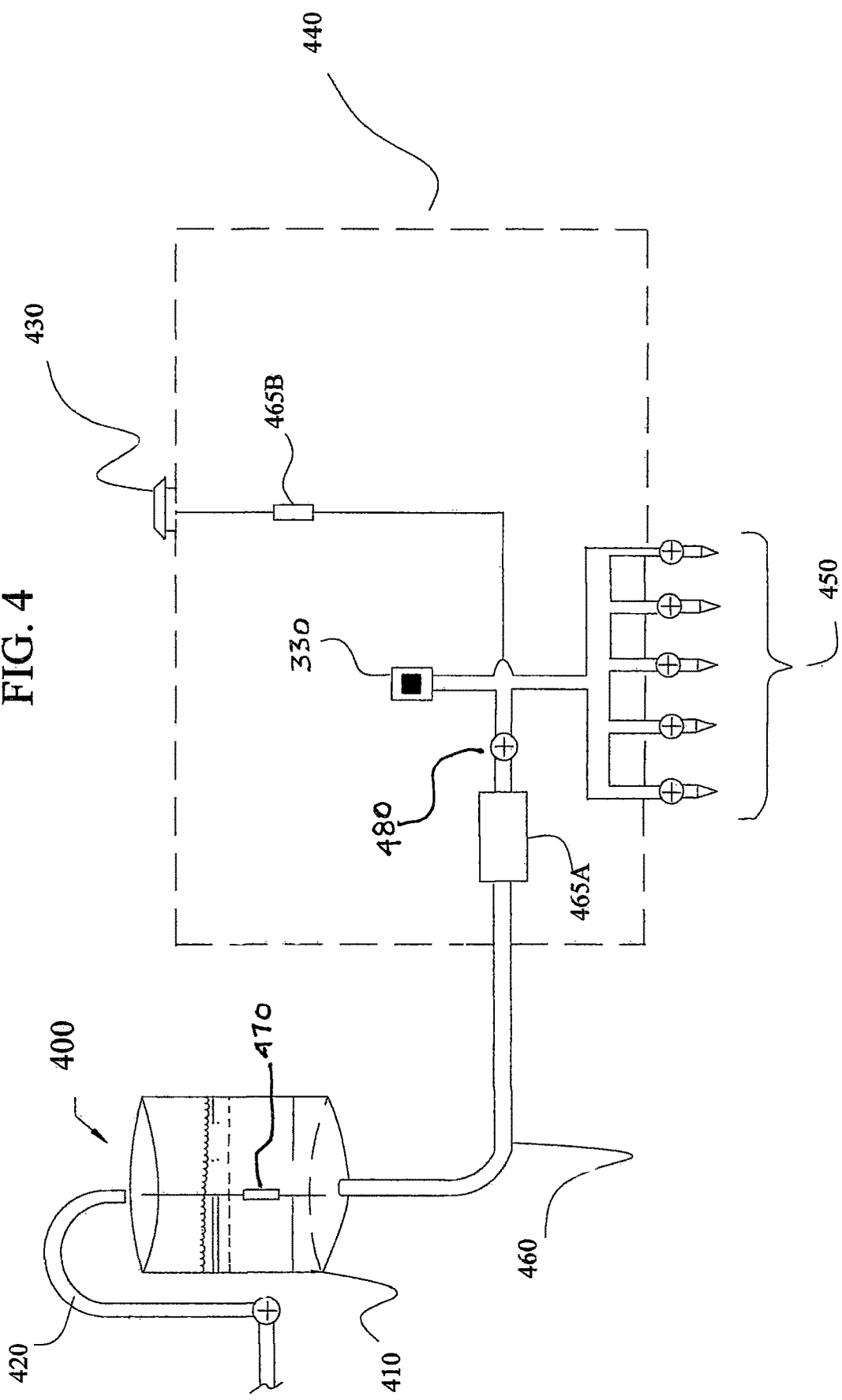
FIG. 4 is an exploded view of the water chemical mixture tank, according to a preferred embodiment of the invention.

In an embodiment, FIG. 4 is a schematic of the chemical storage unit 400 and how it will be ideally supplied with water and or powder by the user for maintenance of the distribution system. The external feed line 420 delivers water to the chemical storage tank 410. The measurement flotation device 470 will measure the amount of water and powder supplied within the chemical storage tank 410. The schematic further illustrates the general portions of embodiment such as pipe 460, heat insulation 465B, the control panel 330, lock-out feature 480, the nozzles 450, exhaust vent 430, and designated area 440.

In an exemplary embodiment, the system will be mounted using a series of mounting points depending on the configuration of the ideal area for the user. For instance, the user will need to inspect the surface space for specific geometry and easily install the Disinfectant Distribution System™ based on geometry. Prior to installing the system, the user will need to mount a bracket system that will be useful for holding the embodiment in place. The bracket system can be designed using at least one railing bracket that can be abutted against the piping of the Distribution System. Once the system has been installed at the target area, the user will route the piping to a remote location to connect to a designated compressor, chemical storage, air system, and power source. The control system 465B can also be easily installed near the compressor as well to ensure that all critical control components are in an isolated area. The overall system will be driven by low voltage electricity but can be designed to be powered by other sources of energy. Alternatively, at FIG. 4, the pipe 460 may be placed in an insulating conduit of relatively large diameter, which may be made of metal or, preferably, plastic to protect the pipe in the event the chemical storage unit 400 is located outside. Heat insulation may also be provided around the length of the entire pipe system depending on use.

Exemplary Embodiments

FIG. 1 is a perspective view of an installed nozzle system of the disinfectant distribution system, according to a preferred embodiment of the invention.

FIG. 2 is a schematic view of a nozzle, according to a preferred embodiment of the invention. According to a preferred embodiment of the invention.

FIG. 3 is a top-view of a disinfectant distribution system, according to a preferred embodiment of the invention. According to the embodiment a distribution system 300

FIG. 4 is an exploded view of the water chemical storage unit, according to a preferred embodiment of the invention. According to the view includes an overall view of the distribution system.

The skilled person will be aware of a range of possible modifications of the various embodiments described above. Accordingly, the present invention is defined by the claims and their equivalents.

The invention claimed is:

1. A disinfectant distribution apparatus for disinfecting an enclosed public area, the disinfectant distribution apparatus comprising:
   a. a body, pipes, detachable cornices, the body having a series of nozzles affixed along said pipes wherein said nozzles are mounted at predetermined intervals along said pipes, at least one control unit, computer control system, internal software, mounts, at least one chemical storage unit, at least one exhaust vent, at least one electrical line extension, and at least one compressor, wherein said apparatus includes a plurality of lock out features for security comprising a software-assisted physical locking mechanism, wherein said at least one compressor and at least one control unit are remotely located at predetermined distances from said body and at least one processor is powered by utilizing at least one form of energy source, wherein said pipes include a one-way valve, wherein said body is configured by utilizing a modular three-part system, wherein said disinfectant distribution apparatus comprises a heat insulation surrounding at least a portion of the length of the pipes, wherein said at least one compressor is powered by a fuel selected from one or more of: diesel, ethanol, methanol, and gasoline.

2. The apparatus of claim 1 wherein said body three-part system is further configured to be manufactured for various sizes and designs based on a targeted space.

3. The apparatus of claim 1 wherein said pipes are designed to be detachable from said mounts.

4. The apparatus of claim 1 wherein said mounts are attached to an upper-side surface of said pipes.

5. The apparatus of claim 4 wherein said mounts are further attached to an existing mounting location in an area to affix said apparatus.

6. The apparatus of claim 1 wherein said at least one compressor is operable by utilizing said at least one energy source, wherein said at least one compressor is not dependent on low voltage energy but rather will be powered by regular or line voltage.

7. The apparatus of claim 1 wherein said at least one chemical storage unit is installed at a predefined distance from said body; and designed to be attached to said pipes for distribution of chemicals.

8. The apparatus of claim 1 wherein said at least one chemical storage unit includes a flotation device for measuring a containment level in said at least one chemical storage unit.

9. The apparatus of claim 8 wherein said at least one chemical storage unit further includes an external feed line configured to a predefined length for delivering disinfectant chemicals.

10. The apparatus of claim 1 wherein said apparatus include a physical lock for security purposes.

11. The apparatus of claim 1 wherein said plurality of lock out features will prevent unauthorized third parties from accessing said computer control system.

12. The apparatus of claim 1 wherein said computer control system is operable by said internal software.

* * * * *